United States Patent [19]

Hawkins et al.

[11] 4,242,121
[45] Dec. 30, 1980

[54] METHOD OF ANTAGONIZING HERBICIDES ON SOYABEAN AND COTTON

[75] Inventors: Alan F. Hawkins, Woodley; Terence Lewis, Bracknell; Ian Jones, Camberley, all of England

[73] Assignee: Imperial Chemical Industries Limited, London, England

[21] Appl. No.: 967,880

[22] Filed: Dec. 8, 1978

Related U.S. Application Data

[63] Continuation-in-part of Ser. No. 784,638, Apr. 4, 1977, abandoned.

[30] Foreign Application Priority Data

Apr. 8, 1976 [GB] United Kingdom ............... 14355/76

[51] Int. Cl.² .......................... A01N 9/22; A01N 9/24
[52] U.S. Cl. ............................ 71/93; 71/92; 71/94; 71/120; 71/115; 71/116
[58] Field of Search .................. 71/92, 115, 116, 120, 71/93, 94

[56] References Cited

U.S. PATENT DOCUMENTS

| | | | |
|---|---|---|---|
| 3,928,416 | 12/1975 | Bayer et al. | 71/116 X |
| 3,979,437 | 9/1976 | Theissen | 71/115 X |

FOREIGN PATENT DOCUMENTS 50-58228  5/1975  Japan .
50-71826  6/1975  Japan .

*Primary Examiner*—Catherine L. Mills
*Attorney, Agent, or Firm*—Cushman, Darby & Cushman

[57] ABSTRACT

Method of protecting legumes and cotton from herbicidal damage using a compound of formula:

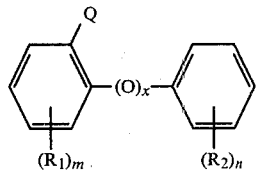

wherein $R_1$ and $R_2$ are hydrogen, halogen, alkoxy, alkyl, trihalomethyl, amino or hydroxy, Q is carboxy, x is 1, m is 1 or 2, and n is 1 or 2.

6 Claims, No Drawings

METHOD OF ANTAGONIZING HERBICIDES ON SOYABEAN AND COTTON

This application is a continuation-in-part application based on U.S. patent application Ser. No. 784,638 (filed Apr. 4, 1977) now abandoned.

This invention relates to a composition suitable for antagonising (or safening) herbicides. In this art, such antagonism is sometimes referred to as an antidote effect.

A considerable amount of effort has been expended in the agricultural industry in developing selective herbicides, i.e. herbicides which will kill weeds in preference to the desired crop. Many of these herbicides are however unsuitable for a certain crop because, while they kill the weeds in the desired way, they also have undesirable phytotoxic effects on that crop. There is thus clearly as demand for compounds which will reduce this phytotoxic effect on the crop without significantly affecting the herbicidal effect on the weeds. Two antidotes have been developed which have the effect of reducing the phytotoxicity of EPTC (Eptam) towards maize thus allowing it to be used with greater safety in this crop. The herbicidal effectiveness on weed species is apparently not impaired. These compounds are Protect (1,8-naphthalic dianhydride) and N,N-diallyldichloroacetamide. However, Protect has the disadvantage that it must be applied as a seed dressing and so commits the farmer to using a particular herbicide later in the cultivation of the crop.

We have now found a class of compounds which antagonise on legumes (especially soyabean) and cotton the herbicidal effect of for example substituted urea and triazine herbicides, e.g. diuron and atrazine, with little or no adverse effect on the herbicidal activity against most weeds. The herbicides which can be antagonised in this way are those which are taken up by a plant from the soil but which are translocated to a main herbicidal site of action within the foliage of the plant. The herbicides which can be antagonised are often those which operate by interfering with part of the photosynthetic system of the plant.

The invention therefore provides a method of selectively controlling weeds in a crop locus, the crop being a legume or cotton, which method comprises applying to the crop locus prior to the emergence of the crop, either successively (in either order) or together, (a) a herbicide which is capable of being taken up by a plant from the soil but which is capable of being translocated to a main hericidal site of action within the foliage of the plant, and (b) a compound of general formula (I):

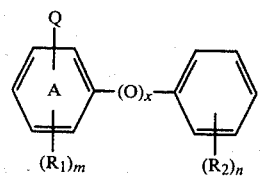

wherein each of $R_1$ and $R_2$, which may be the same or different, is hydrogen, halogen, alkoxy (e.g. lower alkoxy), alkyl (e.g. lower alkyl), trihalomethyl, cyano, acyl (e.g. acetyl or propionyl), alkoxycarbonyl (e.g. lower alkoxycarbonyl), amino or hydroxy, Q is carboxy or a salt or ester thereof or Q is formyl, x is 0 or 1, m is an integer of 1 to 4 (especially 1 or 2) and n is an integer of 1 to 5 (especially 1, 2 or 3), whereby the herbicidal effect on the weeds is not reduced below an effective level.

When m and/or n are greater than 1, the groups $R_1$ and/or the groups $R_2$ may be the same or different.

The alkyl and alkoxy groups can be straight or branched chain groups; examples are methyl, ethyl, propyl (n- or isopropyl), butyl (n-, iso- or t-butyl), amyl, methoxy, ethoxy or propoxy. The term "lower alkoxy" and "lower alkyl" refer to groups having 1 to 6 carbon atoms. The halogen atom can be fluorine, chlorine, bromine or iodine. A suitable trihalomethyl group is trifluoromethyl and a suitable alkoxy-carbonyl group is methoxy- or ethoxy-carbonyl. Suitable salts are the alkali metal (e.g. sodium or potassium) salts, alkaline earth metal (e.g. calcium) salts, ammonium salts or amine salts. The amine is a suitable mono- or di-alkylamine, e.g. dimethylamine, diethylamine or isopropylamine; an alternative is a mixture of higher mono-alkylamines e.g. Synprolan 35 (see below). Suitable esters are those wherein Q is alkoxy-carbonyl (e.g. methoxy- or ethoxy-carbonyl).

The position of the carboxy or formyl group in Ring A is not particularly critical. However, those compounds wherein the carboxy is in the meta-position but which are otherwise unsubstituted are more active antagonists than those wherein this group is in the ortho-position. In general, increasing the substitution on Rings A and B improves the antagonist activity.

Examples of particularly suitable safener compounds are 3-chloro-6-(2'-methylphenoxy)benzoic acid (Compound 8 in Table I below; m.p. 124° C.), 3-chloro-6-(2',5'-dimethylphenoxy) benzoic acid (Compound 21; m.p. 131°–132° C.), 3-chloro-6-(3',5'-dimethylphenoxy)-benzoic acid (Compound 22; m.p. 170°–17° C.), 3-iodo-6-phenylbenzoic acid (Compound 94; m.p. 156°–157° C.), 3-chloro-6-(2'-chlorophenoxy)benzoic acid (Compound 6), 3-chloro-6-(3'-chlorophenoxy)benzoic acid (Compound 5; m.p. 122°–123° C.), 3-chloro-6-(2'-methoxyphenoxy)benzoic acid (Compound 14), 3-chloro-6-(3'-methoxyphenoxy)benzoic acid (Compound 15; m.p. 105° C.), 3-chloro-6-(3',5'-dichlorophenoxy)benzoic acid (Compound 16; m.p. 146°–147° C.), 3-chloro-6-(3'-methoxy-5'-chlorophenoxy)benzoic acid (Compound 27; m.p. 152° C.), 4-chloro-6-(3',5'-dimethylphenoxy)benzoic acid (Compound 55; m.p. 170°–171° C.), 3-chloro-6-phenylbenzoic acid (Compound 91). Of these compounds, Compounds 5, 8, 15, 16, 21, 22, 27, 55 and 94 are novel compounds and as such form part of the present invention.

The compounds can be prepared by one of the following processes:

(1) A halobenzoic acid and a phenol can be condensed in the form of their alkali metal salts in the presence of a copper catalyst, and/or a cuprous salt to give a phenoxybenzoic acid. An excess of the phenol or a suitable high boiling solvent can be used as reaction medium. The reaction can be conducted at 110° to 250° C., for example 120° to 250° C.

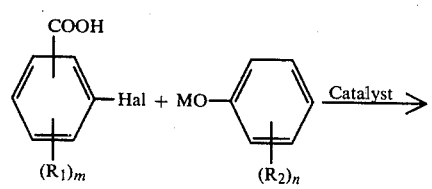

-continued

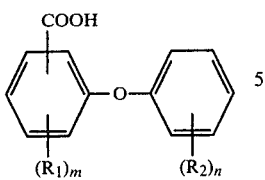

wherein M is an alkali metal cation and Hal is halogen, e.g. chlorine.

(2) Methylhalobenzene can be reacted with an alkali metal salt in the presence of a metallic copper and/or a cuprous salt, as above. The resulting methyl diphenyl ether can then be oxidised (e.g. with potassium permanganate) to give the corresponding phenoxybenzoic acids.

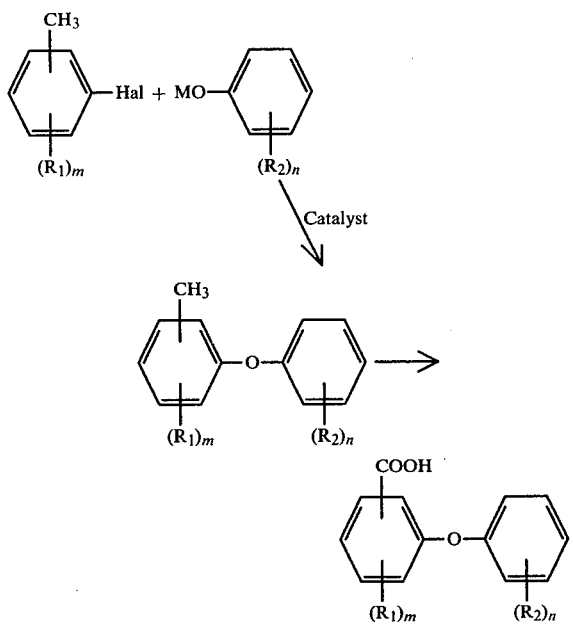

(3) The phenoxybenzoic acids and phenylbenzoic acids can be prepared by reaction of diphenyl ethers or diphenyls with oxalyl chloride and aluminium chloride, at −10° to +25° C. in an inert solvent e.g. carbon tetrachloride or carbon disulphide.

(4) Diphenyl ethers or diphenyls can be reacted with acetyl halides or anhydrides in the presence of aluminium chloride at −10° to +25° C. in an inert solvent to give the acetyldiphenyl ethers or acetyldiphenyls which can be converted to the phenoxybenzoic acids or phenylbenzoic acids by oxidation e.g. with a metal hypohalite (e.g. hypochorite) or sodium dichromate:

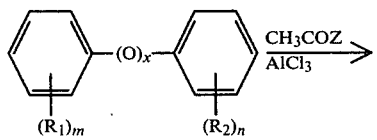

-continued

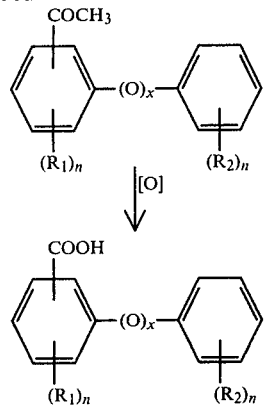

wherein Z is halogen or carboxylic acyloxy (e.g. acetoxy).

(5) The halophenoxybenzoic acids or halophenylbenzoic acids can be prepared by halogenation of the phenoxybenzoic acids or esters (or their diphenyl ether precursors) or of the phenylbenzoic acids or esters using elemental halogens or other halogenating agents, e.g. sulphuryl chloride, with or without a catalyst such as titanium tetrachloride.

(6) Esters can be formed by known methods from the alcohol and the phenoxybenzoic or phenylbenzoic acid using an acid (e.g. hydrogen chloride) or a base (e.g. a metal alkoxide) as the catalyst. The salts can also be prepared in known manner.

The compounds of general formula (I) wherein x is 0, i.e. the diphenyl compounds, can also be prepared by the following processes:

(7) A halobenzoic acid ester can be reacted with a halobenzene at 180°–250° C. (e.g. 200°–250° C.) in the presence of a copper catalyst and in the presence or absence of an inert solvent to give the phenylbenzoic acid ester, which can if desired by hydrolysed to the free acid or a salt thereof.

The reaction involved is:

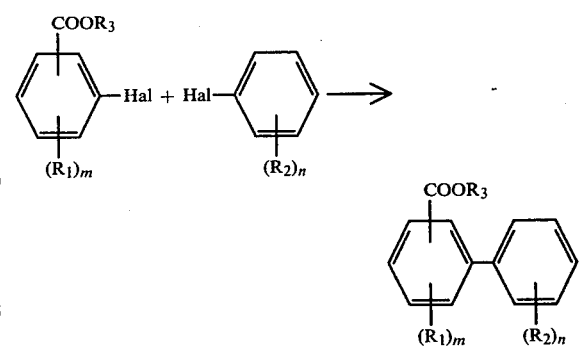

wherein $R_3$ is alkyl.

(8) Analogously to process (2) above, the following reaction can be performed

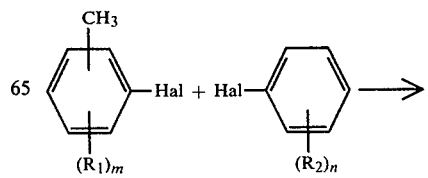

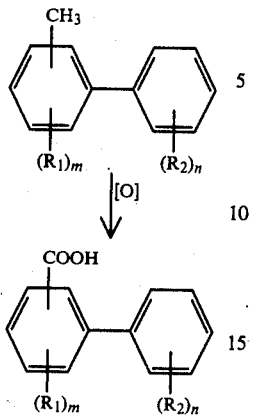

(9) An aminobenzoic acid ester can be reacted with a substituted or unsubstituted benzene (which can also act as the solvent for the reaction) in the presence of amyl nitrite to give a phenylbenzoic acid ester which can if desired by hydrolysed to the free acid or a salt thereof.

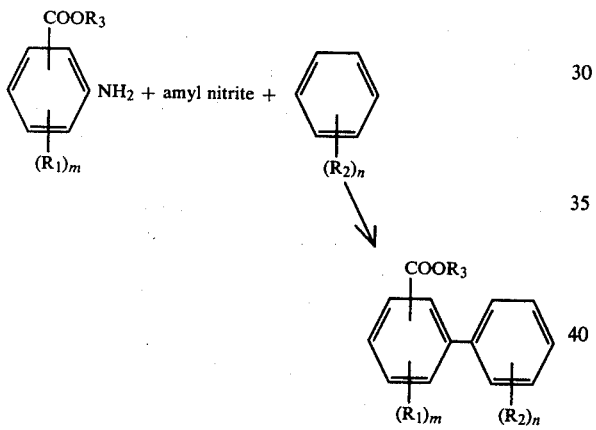

The aldehydes, i.e. the compounds of general formula (I) wherein Q is formyl, can be prepared in known manner by oxidation of the corresponding methyl- or bromomethyl-substituted compounds or by reduction of the corresponding acid halide. Alternatively they can be prepared by the Vilsmeier-Haack Reaction in which a diphenyl ether or a diphenyl is reacted with phosphorus oxychloride in the presence of dimethylformamide and then the intermediate product so formed is hydrolysed.

While the legume treated is preferably soyabean, another possible legume is the French bean.

Suitable herbicides are the following:

(1) Triazine herbicides, e.g. simazine, atrazine, ametryne, terbutryne, cyanazine, prometryne and aziprotryne.

(2) Urea herbicides, e.g. monuron, diuron, neburon, fluometuron, monolinuron, linuron, methabenzthiazuron, nururon, and chlortoluron.

(3) Halopyridines of general formula:

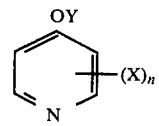

wherein X is hydrogen or halogen (e.g. fluorine, chlorine or bromine), n is an integer of 1 to 4 and Y is hydrogen or aralkyl (e.g. benzyl). Examples of such herbicidal compounds are haloxydine (3,5-dichloro-2,6-difluoro-4-hydroxypyridine) and 3,5,6-tribromo-2-fluoro-4-hydroxypyridine.

(4) Triazinediones as disclosed in Belgian Patent Specification No. 799932 (the disclosure of which Specification is incorporated herein by reference); examples of such compounds have the general formula:

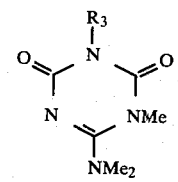

wherein $R_3$ is $C_{3-6}$ alkyl or optionally methyl-substituted $C_{5-8}$ cycloalkyl. A specific example is Velpar (1-cyclohexyl-3-methyl-4-dimethylamino-1,3,5-triazine-2,6-dione).

(5) Pyridones as disclosed in French Patent Specification No. 2283130 (the disclosure of which Specification is incorporated herein by reference); examples of such compounds have the general formula:

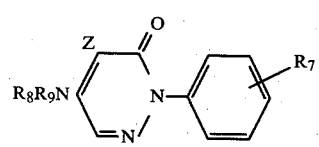

wherein each of $R_4$ and $R_5$, which may be the same or different, is halogen, $C_{1-3}$ alkyl or alkoxy or trifluoromethyl, each of x and y, which may be the same or different, is 0, 1 or 2, and $R_6$ is $C_{1-3}$ alkyl, $C_{2-3}$ alkenyl, acetoxy or methoxy.

A specific example is 1-methyl-3-phenyl-5-(3-trifluoromethylphenyl)-4(1H)-pyridone.

(6) Pyridazinones of general formula:

wherein Z is halogen (e.g. fluorine, chlorine or bromine), $R_7$ is hydrogen or trihalomethyl (e.g. trifluoromethyl), and each of $R_8$ and $R_9$ which may be the same or different, is hydrogen or alkyl. Examples are:

metfluorazone

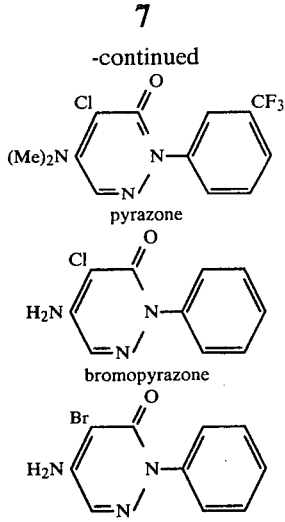

pyrazone bromopyrazone

The herbicide antagonists can be applied to the crops together with the herbicide or alternatively before or after the application of the herbicide. The antagonists are applied to the soil before the emergence of the crop (pre-emergence application).

The rate at which the antagonist is applied will depend on a number of factors, for example the identity of the particular antagonist selected, the herbicide to be treated and the particular crop and weed to be treated. However, generally there is used an amount of 2 to 20, preferably 5 to 10, kgs/hectare. The skilled worker in the art will readily be able to ascertain suitable application rates by routine standardised procedures without undue experimentation.

The compounds of general formula (I) can have, in addition to their ability to antagonise a herbicide's effect on a crop, also the ability to enhance the herbicidal effect on weeds, or even kill weeds in the absence of the herbicide.

The antagonist compounds are preferably applied in the form of a composition comprising the compound, and a carrier comprising a solid or liquid diluent and preferably a surface active agent, and optionally the herbicide. Compositions comprising the antagonist compounds and the herbicide form part of the present invention.

The compositions can be both dilute compositions, which are ready for immediate use, and concentrated compositions, which require dilution before use, usually with water. Preferably the compositions contain 0.01% to 90% by weight of the antagonist compound.

Dilute compositions ready for use preferably contain 0.01 to 2% by weight of antagonist compound, while concentrated compositions may contain 20 to 90% preferably 20 to 70%, by weight of antagonist compound.

Solid compositions may be in the form of a powder containing a powdered solid diluent, for example, Fuller's earth, powdered kaolin, gypsum, chalk and kieselguhr. Such solid compositions may be applied as foliar dusts. The solid compositions can be in the form of a seed dressing in which case they can comprise an agent (e.g. a mineral oil) for assisting the adhesion of the composition to the seed.

Liquid compositions may comprise a solution or dispersion of the antagonist compound in water optionally containing a surface-active agent, or may comprise a solution or dispersion of the antagonist compound in a water-immiscible organic solvent which is dispersed as droplets in water.

The surface-active agent can be for example the products of condensation of ethylene oxide with alkyl-substituted phenols such as octyl- and nonyl-phenol; sorbitan monolaurate; oleyl alcohol; and propylene oxide polymer. A particular example of such a condensation product is Lissapol. Other examples are calcium dodecylbenzenesulphonate, and calcium, sodium and ammonium lignosulphonates.

The concentrated composition preferably comprises the antagonist compound finely divided and dispersed in water in the presence of a surface-active agent and a suspending agent. Preferred suspending agents are those which impart thixotropic properties to, and increase the viscosity of, the concentrate.

Examples are hydrated colloidal mineral silicates, such as montmorillonite, beidellite, nontronite, hectorite, saponite and saucorite. Bentonite is especially preferred. Other suspending agents are cellulose derivatives and polyvinyl alcohol.

The invention is illustrated by the following Examples wherein the temperatures are given in degrees Centigrade and the parts and percentages are by weight unless specified otherwise.

The tests for herbicide antagonism were preformed as follows:

METHOD 1 (SAND-NUTRIENT SOLUTION CULTURE)

Seeds of the Amsoy variety of soyabean were either soaked in distilled water for 1 hour, then spread between sheets of damp filter paper and placed in an incubator at 22° for 48 hours, or were sown as dry seed. These were sown in plastic plant pots (diameter 7.6 cm) filled with washed silver sand, grade 8/16.

The pots were initially irrigated with 50 ml of Nutrient Solution (see below). The plants were maintained on a regime of nutrient solution every third day, distilled water being added on the days between.

The plants were grown in a controlled environment chamber giving:

Day 12½ or 16 hours. Temperature 27°, relative humidity 70%±5%

Night 11½ or 8 hours. Temperature 24°, relative humidity 70%±5%

During the day the plants were illuminated at 25,000 lux using cool white fluorescent lamps. They were treated 6 days after sowing (approximately 48 hours after emergence) by applying 40 ml of a drench to the surface of the sand in each pot. The drench contained the herbicide, typically as the commercial formulation, ± the test compound formulated either in a 2% solution of Dispersol T (a mixture of sodium sulphate and a condensate of the sodium salt of naphthalene sulphonic acid and formaldehyde) or as an aqueous solution of an appropriate salt. Application rates were expressed in terms of p.p.m. of test compound in final pot solution.

The plants were visually assessed for injury at usually 13 days, using a 0–9 linear scale where 0=no damage, 9=complete kill.

One or two replicates were normally set up for each treatment and where there were two replicates the results quoted represent the mean of the two replicates.

Nutrient Solution:
$KNO_3$ —0.656 g/l
$Ca(NO_3)_2$—0.656 g/l
$NH_4H_2PO_4$—0.115 g/l MgSO$_4$.7H$_2$O—0.49 g/l
Fe/EDTA* —1 ml/l
H$_3$BO$_3$—3.5 mg/l
MnCl$_2$.4H$_2$O—2.26 mg/l
CuSO$_4$.5H$_2$O—0.1 mg/l
ZnSO$_4$.7H$_2$O—0.275 mg/l
(NH$_4$)$_6$Mo$_7$O$_{24}$.4H$_2$O—0.825 mg/l

*26.1 g of EDTA dissolved in 286 ml of 1 N KOH. 24.9 g FeSO$_4$ added, made up to 1 liter with distilled water and aerated for 3 hours before use.

METHOD 2 (GLASSHOUSE POT TESTS)

Crop seeds and weed seeds were sown at appropriate depths in, respectively, plastic pots (diameter 10 cm) or cardboard punnets (length 12 cm, width 8 cm, depth 6 cm) filled with compost comprising 50% of natural loam, 25% of grit, and 25 % of vermiculite (percentages by volume). Test compounds were sprayed onto the soil surface preemergence at a volume of 200 l/ha using a travelling boom laboratory sprayer. Herbicides were applied as commercial formulations, and the antagonists as an aqueous solution of an appropriate salt. Where it was desired to apply a mixture of herbicide plus antagonist, one ingredient was sprayed on and then immediately afterwards the other was sprayed but if desired the ingredients can be mixed prior to spraying.

The plants were grown under illuminated glasshouse conditions, top watered as required and visually assessed usually after 21 days for damage, and generally using a 0–9 linear scale as indicated above.

Two replicates were normally used for each treatment; in the Tables, a mean of the replicates is given.

METHOD 3

All plants were grown in compost in disposable cardboard trays. Weed and crop seeds were sown at varying depths according to their requirements (but none > 2.5 cm deep). The soil surface was sprayed with a mixture of the herbicide and the antagonist and the surface was then covered almost immediately with a layer (1–2 mm) of sieved, untreated soil. During each experiment the plants are watered manually as required.

All assessments were visual based on a 0–9 scale where 0 = 10% damage and 9 = 90–100% kill.

EXAMPLE 1

3-Chloro-6-(3'-chlorophenoxy)benzoic Acid

To a solution of 2,5-dichlorobenzoic acid (5.0 g) and m-chlorophenol (3.35 g) in dry toluene (100 mls) was added sodium hydride (1.25 g) under dry nitrogen. Cuprous bromide (3.0 g) was then added and the mixture stirred under reflux for 3 hrs. The toluene was then removed by distillation under reduced pressure and the residue acidified with dilute hydrochloric acid and extracted with diethyl ether. The ethereal extracts were then washed with water and dried over magnesium sulphate. The ether was then removed under reduced pressure and the residue was crystallised from n-hexane to give the title compound.

EXAMPLE 2

3-Chloro-6-(3-trifluoromethylphenoxy)benzoic Acid 2,5-Dichlorobenzoic acid (5 g) and 3-trifluoromethylphenol (4.24 g) were dissolved in xylene and the solution placed under dry oxygen-free nitrogen. Sodium hydride (1.25 g) was slowly added and when effervescence had ceased, cuprous bromide was added and the solution or suspension refluxed for 6 hours. The xylene was removed by low pressure distillation. The solid residue was treated with water and acidified with dilute hydrochloric acid. The resulting oil was extracted into diethyl ether and the ether removed by low pressure distillation to give a light yellow solid which was recrystallised from diethyl ether/petroleum ether to give the title compound (2.7 g), mp, 124° C.

EXAMPLE 3

3-Chloro-6-(3,5-diisopropylphenoxy)benzoic Acid 2,5-dichlorobenzoic acid (5 g) and 3,5-diisopropylphenol (4.66 g) were dissolved in dry xylene and the solution placed under dry oxygen-free nitrogen. Sodium hydride (1.25 g) was added as a suspension in petroleum ether. Cuprous bromide was added and the solution refluxed for 5 hours and cooled. The xylene was removed by low pressure distillation. The remaining solid was acidified with dilute hydrochloric acid and extracted with diethyl ether. The ethereal layer was separated, dried and distilled under low pressure to give an oil. The oil was dissolved in petroleum ether (30°–40° ). Standing gave a crystalline solid, which was recrystallised from hexane to give the title compound (4.3 g), mp 129°–130° C.

EXAMPLE 4

3-Chloro-6-(3'-methylphenoxy)benzoic Acid

Sodium (2.41 g) was dissolved in methanol and the solution placed under dry oxygen-free nitrogen. 2,5-Dichlorobenzoic acid (10 g), m-cresol (30 g) and activated copper powder (0.5 g) were added and the methanol removed by distillation. The temperature was increased to 180° with vigorous stirring and this temperature was maintained for 3 hours. The solution was cooled and steam distilled to remove the excess phenol. The resulting solution was filtered, cooled to room temperature and acidified with hydrochloric acid to give an oil. The oil slowly solidified; it was filtered off, dried, and washed with petroleum ether (30°–40° ). It was recrystallised at −10° from diethyl ether/petroleum ether (30°–40° ) to give, as a grey solid, the title compound (4.5 g), mp 124°–125° C.

EXAMPLE 5

4-(4'Methylphenoxy)benzoic Acid

4-Methyldiphenyl ether (21.5 g) in carbon disulphide (120 mls) was mixed with aluminium chloride (18.4 g) and a solution of acetyl chloride (10.0 g) in carbon disulphide (25 mls) was added dropwise with stirring at 0°. The mixture was then stirred at room temperature for 4 hours and then refluxed for 3 hours. The solvent was then evaporated off, and the residue acidified with 2 N-hydrochloric acid and then extracted with diethyl ether. The ethereal extracts were washed with water and dried over magnesium sulphate. The solvent was then evaporated off and the residue recrystallised from n-hexane to give 4-(4'-methylphenoxy)acetophenone, mp 58°.

Bromine (15.6g) was added dropwise with stirring to a solution of sodium hydroxide (14.0 g) in water (70 mls) at 0°. This mixture was then added to the above intermediate at 35° to 45°. After stirring for 0.25 hours at this temperature, water (350 mls) was added and the mixture acidified with concentrated hydrochloric acid. The white precipitate which formed was then filtered off and recrystallised from methanol to give the title compound, mp 175°.

EXAMPLE 6

3-(4'Bromophenoxy)benzoic Acid

Bromine (2.6 mls) was added dropwise to a mixture of methyl 3-phenoxybenzoate (10.5 g) and titanium tetrachloride (0.2 mls) with stirring at 110°. When hydrogen bromide ceased to be evolved, the mixture was cooled and extracted with diethyl ether. The ethereal extracts were then washed with a saturated solution of sodium bicarbonate in water and dried over magnesium sulphate. The ether was then evaporated off and the residue recrystallised from petroleum ether (40°–60°) to give methyl 3-(4'-bromophenoxy) benzoate, mp 68°–69° C.

This intermediate (5 g) was mixed with 20% caustic soda solution (40 mls) and the mixture refluxed for 3 hours. The cooled mixture was then acidified with concentrated hydrochloric acid and the resulting precipitate filtered off and recrystallised from toluene/petroleum ether (100°–120°) to give the title compound, mp 171°–173° C.

EXAMPLE 7

5-Chloro-2-(2'-methylphenoxy)benzaldehyde

Sulphur (0.1 g) and quinoline (0.6 g) were refluxed for 5 hours and then xylene (70 mls) was added to give a catalyst poison.

5-Chloro-2-(2'-methylphenoxy)benzoyl chloride (5.0 g) was dissolved in toluene (50 mls) and the catalyst poison (0.7 mls) followed by the catalyst (0.7 g; 5% palladium on barium carbonate) were added. Hydrogen was then bubbled through the stirred mixture at 100° until no more hydrogen chloride was evolved. The mixture was then cooled to 40°. Animal charcoal (0.2 g) was added and the mixture was filtered through kieselguhr. Evaporation of the solvent from the filtrate gave an oil which was purified by distillation under reduced pressure to give the title compound as a low melting point solid (mp 45°–46°).

EXAMPLE 8

2-Bromo-5-phenoxybenzaldehyde

N-Bromosuccinimide (16.2 g) was added to a solution of 2-bromo-5-phenoxytoluene (15.3 g) in carbon tetrachloride (50 mls) containing benzoyl peroxide (0.05 g) and the mixture refluxed for ten hours. The precipitate of succinimide was filtered off and the filtrate washed with N-sodium hydroxide solution followed by water. Drying over magnesium sulphate and evaporation of the solvent gave, as a light yellow oil, 4-phenoxy-2-bromomethylphenyl bromide.

Sodium bicarbonate (2.94 g) was added to a solution of this intermediate (10.26 g) in dimethyl sulphoxide (20 mls) and the mixture stirred at 120° for 3 hours. After cooling the reaction mixture, water (50 mls) was added and the mixture extracted with diethyl ether. Sodium metabisulphite (8.0 g) in water (15 mls) and ethanol (12 mls) were then added to the ethereal extracts. The mixture was then stirred for 0.5 hours at 22° and the white precipitate filtered off and washed with ethanol. The solid was then shaken with 10% sodium hydroxide solution and extracted with diethyl ether. The ethereal extracts were then washed with water and dried over anhydrous magnesium sulphate. Evaporation of the solvent gave, as a light yellow oil, the title compound, bp 138°–140°/0.1 mm.

EXAMPLE 9

5-Iodo-2-phenylbenzoic Acid

Concentrated sulphuric acid (12 mls) was added dropwise to methyl 2-amino-5-iodobenzoate (42.3 g), glacial acetic acid (64 mls) and benzene (120 mls) at 10°. Amyl nitrite (81.6 mls) was then added dropwise over 10 minutes at 10° followed by potassium carbonate (33.6 g). The mixture was stirred at 10° for 4 hours and then refluxed for 2 hours. The mixture was then filtered, and the filtrate washed with water and dried over magnesium sulphate. The solvent was evaporated off and the resulting methyl 5-iodo-2-phenylbenzoic acid purified by distillation under reduced pressure.

This intermediate (15 g) was mixed with 20% sodium hydroxide solution (100 mls) and the mixture refluxed for 3 hours. The cooled mixture was then acidified with concentrated hydrochloric acid and the resulting precipitate filtered off and recrystallised from ethanol to give the title compound.

EXAMPLE 10

Various compounds of general formula (I) were tested on soyabean for their antagonist effect on diuron. Method 1 was used. In Table I below, Column C indicates the effect of diuron alone, Column A indicates the diuron effect produced by the mixture of the safener and the herbicide and Column B indicates the total phytotoxic effect of the mixture.

TABLE I

| NO | Q | x | $(R_1)_m$ | $(R_2)_n$ | RATE (p.p.m.) 40 | | | 20 | | | 10 | | | 4 | | |
|---|---|---|---|---|---|---|---|---|---|---|---|---|---|---|---|---|
| | | | | | A | B | C | A | B | C | A | B | C | A | B | C |
| 1 | 2-COOH | 1 | H | H | 1 | 3 | 7.5 | 6 | 6 | 6 | 7.5 | 7.5 | 8.0 | | | |
| | | | | | 4.5 | 5.5 | 8 | 9 | 9 | 7 | | | | | | |
| | | | | | 0.5 | 3.5 | 7.5 | | | | | | | | | |
| | | | | | 0 | 2.5 | 6.5 | | | | | | | | | |
| 2 | 2-COOH | 1 | H | 2-OMe | 0 | 1 | 7 | 6 | 6 | 7.5 | 7.5 | 7.5 | 7.5 | | | |
| | | | | | 6 | 6 | 6 | 6 | 6 | 6 | | | | | | |
| 3 | 2-COOH | 1 | H | 2-Me, 4-Cl | | | | 5 | 5 | 7 | 5 | 5 | 7 | | | |
| 4 | 2-COOH | 1 | 4-Cl | H | | | | 1 | 2 | 8.5 | 8 | 8 | 6 | | | |
| | | | | | | | | 7 | 7 | 6 | 6 | 6 | 7 | | | |
| | | | | | | | | 3 | 3 | 7 | | | | | | |
| 5 | 2-COOH | 1 | 4-Cl | 3-Cl | | | | 2 | 2 | 6 | 5 | 5 | 6 | | | |
| | | | | | | | | 0 | 2 | 8.5 | 0 | 3 | 9 | 9 | 9 | 9 |
| | | | | | | | | 3 | 3 | 7 | 6 | 6 | 7 | | | |
| 6 | 2-COOH | 1 | 4-Cl | 2-Cl | 0 | 3 | 7.5 | 2 | 2 | 6 | 0 | 2.5 | 8 | 5 | 5 | 7.5 |
| | | | | | | | | 8 | 8 | 7 | 6 | 6 | 6 | | | |
| 7 | 2-COOH | 1 | 4-Cl | 2-Br | | | | 0 | 0 | 7 | | | | | | |

TABLE I-continued

| | | | | | RATE (p.p.m.) | | | | | | | | | | |
|---|---|---|---|---|---|---|---|---|---|---|---|---|---|---|---|
| | | | | | 40 | | | 20 | | | 10 | | | 4 | | |
| NO | Q | x | $(R_1)_m$ | $(R_2)_n$ | A | B | C | A | B | C | A | B | C | A | B | C |
| 8 | 2-COOH | 1 | 4-Cl | 2-Me | 0 | 2.5 | 7.5 | 0<br>1<br>0<br>6 | 0<br>1<br>0<br>6 | 7<br>7<br>7<br>7 | 0<br>4<br>6 | 2<br>4<br>6 | 8<br>7<br>7 | 5.5 | 5.5 | 7.5 |
| 9 | 2-COOH | 1 | 4-Cl | 3-Me | | | | 3<br>1 | 3<br>3 | 6<br>8.5 | 5 | 5 | 7 | | | |
| 10 | 2-COOH | 1 | 4-Cl | 4-Me | 3.5<br>1.5 | 5<br>2.5 | 7.5<br>8 | 7<br>7 | 7<br>7 | 6<br>7 | 7.5 | 7.5 | 7.5 | | | |
| 11 | 2-COOH | 1 | 4-Cl | 2-Et | | | | 6<br>3 | 6<br>3 | 9<br>6 | 8<br>9 | 8<br>9 | 7.5<br>9 | | | |
| 12 | 2-COOH | 1 | 4-Cl | 3-CF₃ | | | | 3 | 3 | 7 | 8 | 8 | 7 | | | |
| 13 | 2-COOH | 1 | 4-Cl | 3-i-Pr | | | | 3 | 3 | 7 | 5 | 5 | 7 | | | |
| 14 | 2-COOH | 1 | 4-Cl | 2-OMe | 0 | 3 | 7.5 | 0<br>6<br>7 | 0<br>6<br>7 | 6<br>7<br>7 | 0<br>6.5<br>5 | 1<br>6.5<br>5 | 8<br>7.5<br>7.5 | 7.5 | 7.5 | 7.5 |
| 15 | 2-COOH | 1 | 4-Cl | 3-OMe | 3<br>4 | 3<br>4 | 6<br>7 | 1<br>5 | 1<br>5 | 9<br>6 | 0 | 2 | 9 | | | |
| 16 | 2-COOH | 1 | 4-Cl | 3,5-diCl | | | | 0 | 1 | 7 | 3 | 3 | 7 | | | |
| 17 | 2-COOH | 1 | 4-Cl | 2,6-diCl | | | | 6<br>7 | 6<br>7 | 6<br>7 | 7<br>6 | 7<br>6 | 9<br>6 | | | |
| 18 | 2-COOH | 1 | 4-Cl | 2,4-diCl | 0 | 3.5 | 7.5 | 6<br>7 | 6<br>7 | 6<br>7 | 6<br>8 | 6<br>8 | 8<br>6 | 7.5 | 7.5 | 7.5 |
| 19 | 2-COOH | 1 | 4-Cl | 2,4-diMe | 5<br>2 | 5<br>2 | 6<br>7 | 7<br>6 | 7<br>6 | 8.5<br>6 | | | | | | |
| 20 | 2-COOH | 1 | 4-Cl | 2,3-diMe | | | | 1<br>2<br>7 | 2<br>2<br>7 | 8.5<br>6<br>7 | 6<br>9 | 6<br>9 | 6<br>7 | | | |
| 21 | 2-COOH | 1 | 4-Cl | 2,5-diMe | 0 | 3 | 7.5 | 2<br>1 | 3<br>3 | 6<br>7 | 1.5<br>5 | 3.5<br>5 | 8<br>6 | 6.5 | 6.5 | 7.5 |
| 22 | 2-COOH | 1 | 4-Cl | 3,5-diMe | 0 | 3 | 7.5 | 0<br>0 | 0<br>2 | 7<br>8.5 | 0<br>1 | 2.5<br>1 | 8<br>8.5 | 5.5 | 5.5 | 7.5 |
| 23 | 2-COOH | 1 | 4-Cl | 3,5-diOMe | | | | 0 | 5 | 8 | 4 | 4 | 8 | | | |
| 24 | 2-COOH | 1 | 4-Cl | 3,5-di-i-Pr | | | | 4 | 4 | 7.5 | 3 | 3 | 7 | | | |
| 25 | 2-COOH | 1 | 4-Cl | 2-Cl-5-Me | | | | 1 | 1 | 7 | 4 | 4 | 7 | | | |
| 26 | 2-COOH | 1 | 4-Cl | 2-Me-4-Cl | | | | 0 | 2 | 7 | 8 | 8 | 9 | | | |
| 27 | 2-COOH | 1 | 4-Cl | 3-OMe-5-Cl | | | | 5<br>0 | 5<br>2 | 8<br>9 | 1 | 1 | 9 | | | |
| 28 | 2-COOH | 1 | 4-Cl | 2-Me-3-OMe | | | | 4<br>6 | 4<br>6 | 6<br>7 | 7<br>7<br>7 | 7<br>7<br>7 | 9<br>6<br>7 | | | |
| 29 | 2-COOH | 1 | 4-Cl | 2,3,5-triMe | | | | 5 | 5 | 8 | 9 | 9 | 8 | | | |
| 30 | 2-COOH | 1 | 4-Br | H | | | | 1 | 1 | 7.5 | 6 | 6 | 7.5 | | | |
| 31 | 2-COOH | 1 | 4-Br | 2-Me | | | | 2<br>0<br>3 | 2<br>2<br>3 | 7<br>7.5<br>6 | 6<br>8<br>5 | 6<br>8<br>5 | 7<br>9<br>6 | | | |
| 32 | 2-COOH | 1 | 4-Br | 5-Cl | | | | 1 | 1 | 7.5 | 7 | 7 | 7.5 | | | |
| 33 | 2-COOH | 1 | 4-Br | 2-Cl | | | | 3<br>1<br>5 | 3<br>2<br>5 | 7<br>9<br>6 | 4<br>6 | 4<br>6 | 6<br>7 | 5<br>9 | 5<br>9 | 8<br>9 |
| 34 | 2-COOH | 1 | 4-Br | 5-OMe | | | | 1 | 1 | 7.5 | 8 | 8 | 7.5 | | | |
| 35 | 2-COOH | 1 | 4-Br | 2-OMe | | | | 1 | 1 | 7 | 5 | 5 | 7 | | | |
| 36 | 2-COOH | 1 | 4-Br | 3,5-diMe | | | | 2.5<br>5<br>4 | 2.5<br>5<br>4 | 7.5<br>6<br>7 | 1<br>2<br>5<br>5 | 1<br>2<br>5<br>5 | 5<br>7.5<br>6<br>7 | 8 | 8 | 7.5 |
| 37 | 2-COOH | 1 | 4-I | H | | | | 3 | 3 | 7 | | | | | | |
| 38 | 2-COOH | 1 | 4-I | 2-Me | | | | 4<br>7 | 4<br>7 | 6<br>7 | 5<br>5<br>6 | 5<br>5<br>6 | 6<br>9<br>7 | | | |
| 39 | 2-COOH | 1 | 4-I | 2-Cl | 4<br>3 | 4<br>3 | 6<br>7 | 8<br>3 | 8<br>3 | 9<br>6 | 9 | 9 | 9 | | | |
| 40 | 2-COOH | 1 | 4-Me | 2-Me | 5<br>0 | 5<br>0 | 6<br>7 | 4<br>3 | 6<br>3 | 8.5<br>6 | | | | | | |
| 41 | 2-COOH | 1 | 4-Me | 2-Cl | 2<br>0 | 2<br>0 | 6<br>7 | 6<br>4 | 6<br>4 | 9<br>6 | | | | | | |
| 42 | 2-COOH | 1 | 4-NH₂ | H | 2<br>5 | 5.5<br>5 | 8<br>6 | 6<br>7 | 6<br>7 | 6<br>7 | | | | | | |
| 43 | 2-COOH | 1 | 5-Cl | H | 0<br>5 | 1<br>5 | 6<br>7 | 2<br>4 | 3<br>4 | 8.5<br>6 | 8.5 | 8.5 | 8.5 | | | |

TABLE I-continued

| NO | Q | x | (R₁)ₘ | (R₂)ₙ | RATE (p.p.m.) 40 | | | 20 | | | 10 | | | 4 | | |
|---|---|---|---|---|---|---|---|---|---|---|---|---|---|---|---|---|
| | | | | | A | B | C | A | B | C | A | B | C | A | B | C |
| 44 | 2-COOH | 1 | 5-Cl | 3-Cl | 0 | 3 | 7.5 | 0.5 | 2 | 7.5 | 9 | 9 | 9 | 9 | 9 | 8.5 |
| | | | | | | | | 1.0 | 3 | 8.5 | 6 | 6 | 6 | | | |
| | | | | | | | | 5 | 5 | 6 | 7 | 7 | 7 | | | |
| 45 | 2-COOH | 1 | 5-Cl | 4-Cl | 5 | 6 | 8 | 5 | 5 | 6 | 8.5 | 8.5 | 8 | | | |
| | | | | | 4 | 4 | 6 | 7 | 7 | 7 | | | | | | |
| 46 | 2-COOH | 1 | 5-Cl | 2-Cl | 0 | 3.5 | 7.5 | 4 | 4 | 6 | 4.5 | 5 | 8 | 6.5 | 6.5 | 7.5 |
| | | | | | | | | | | | 7 | 7 | 6 | | | |
| 47 | 2-COOH | 1 | 5-Cl | 4-Me | 2 | 5 | 7.5 | 7.5 | 7.5 | 7.5 | 5.5 | 5.5 | 7 | 8 | 8 | 7.5 |
| | | | | | 1.5 | 4 | 8 | 6 | 6 | 6 | | | | | | |
| 48 | 2-COOH | 1 | 5-Cl | 3-Me | 1.5 | 1.5 | 8 | 4 | 4 | 6 | 8 | 8 | 8 | | | |
| | | | | | 2 | 2 | 6 | 7 | 7 | 7 | | | | | | |
| | | | | | 7 | 7 | 7 | | | | | | | | | |
| 49 | 2-COOH | 1 | 5-Cl | 2-Me | 0 | 3 | 7.5 | 5 | 5 | 6 | 1 | 3 | 8 | 7 | 7 | 7.5 |
| | | | | | | | | 8 | 8 | 7 | 6 | 6 | 7.5 | | | |
| 50 | 2-COOH | 1 | 5-Cl | 3-OMe | 0 | 0 | 6 | 6 | 6 | 9 | 9 | 9 | 9 | | | |
| | | | | | 3 | 3 | 7 | 3 | 3 | 8 | | | | | | |
| 51 | 2-COOH | 1 | 5-Cl | 2-OMe | | | | 1 | 3 | 8 | 6 | 6 | 6 | 8 | 8 | 8.5 |
| | | | | | | | | 4 | 4 | 6 | 6 | 6 | 6 | | | |
| 52 | 2-COOH | 1 | 5-Cl | 2-OEt | 0 | 0 | 8 | 7 | 7 | 6 | 7.5 | 7.5 | 8 | | | |
| | | | | | | | | 9 | 9 | 7 | 5 | 5 | 6 | | | |
| 53 | 2-COOH | 1 | 5-Cl | 2,4-diCl | 0 | 2 | 8 | 5 | 5 | 6 | 6 | 6 | 8 | | | |
| | | | | | | | | 8 | 8 | 7 | 6 | 6 | 6 | | | |
| 54 | 2-COOH | 1 | 5-Cl | 2,4-diMe | 3 | 3 | 6 | 8.5 | 8.5 | 9 | | | | | | |
| | | | | | 8 | 8 | 7 | | | | | | | | | |
| | | | | | | | | 0 | 3.5 | 8 | 1.5 | 3.5 | 8 | | | |
| 55 | 2-COOH | 1 | 5-Cl | 3,5-diMe | 0 | 3 | 7.5 | 0 | 1 | 5 | 2 | 2 | 8 | 6.5 | 6.5 | 7.5 |
| | | | | | | | | 0 | 0 | 8 | 3 | 5.5 | 7.5 | 7.5 | 7.5 | 7.5 |
| | | | | | | | | 0 | 3 | 8 | 3.5 | 3.5 | 8 | | | |
| 56 | 2-COOH | 1 | 5-Cl | 2,5-diMe | 0 | 3 | 7.5 | 4 | 4 | 6 | 3 | 4.5 | 8 | 7 | 7 | 7.5 |
| | | | | | | | | 6 | 6 | 7 | 6 | 6 | 6 | | | |
| 57 | 2-COOH | 1 | 6-Me | 2-Cl | | | | 9 | 9 | 9 | | | | | | |
| 58 | 2-COOH | 1 | 6-Cl | 2,5-diMe | 0 | 3 | 7.5 | 3 | 3 | 6 | 5.5 | 5.5 | 8 | 7.5 | 7.5 | 7.5 |
| | | | | | | | | 6 | 6 | 7 | 5 | 5 | 6 | | | |
| 59 | 2-COOH | 1 | 3-OMe-4-Cl | H | | | | 0 | 4 | 8.5 | | | | | | |
| 60 | 2-COOH | 1 | 3-OMe-4-Cl | 2-Me | | | | 4 | 7 | 8 | 8 | 8 | 8 | | | |
| 61 | 2-COOMe | 1 | H | H | 0.5 | 4 | 8 | 7 | 7 | 6 | 8 | 8 | 8 | | | |
| | | | | | 2.5 | 4 | 8 | 6 | 6 | 7 | | | | | | |
| 62 | 2-COOMe | 1 | H | 2-Me | 6 | 6 | 8 | 6 | 6 | 6 | | | | | | |
| | | | | | 5 | 5 | 6 | 7 | 7 | 7 | | | | | | |
| | | | | | 7 | 7 | 7 | | | | | | | | | |
| 63 | 2-COOMe | 1 | H | 4-OH | 7.5 | 7.5 | 8 | | | | | | | | | |
| 64 | 2-COOMe | 1 | H | 4-Me | 6.5 | 6.5 | 8 | 5 | 5 | 6 | | | | | | |
| | | | | | 4 | 4 | 6 | 8 | 8 | 7 | | | | | | |
| 65 | 2-COOEt | 1 | 4-Cl | 2-Me | | | | 6 | 6 | 7 | 7 | 7 | 7 | | | |
| 66 | 2-COO-n-Bu | 1 | 4-Cl | 2-Me | | | | 6 | 6 | 7 | 6 | 6 | 7 | | | |
| 67 | 3-COOH | 1 | H | H | 0 | 3 | 7.5 | 6 | 6 | 9 | 4.5 | 5 | 8 | 8 | 8 | 7.5 |
| | | | | | 0 | 2 | 6.5 | 6 | 6 | 6 | | | | | | |
| 68 | 3-COOH | 1 | 4-OH | H | 2 | 5 | 7.5 | | | | | | | | | |
| | | | | | 7 | 7 | 8 | | | | | | | | | |
| 70 | 3-COOH | 1 | 4-Br | H | | | | 6 | 6 | 7.5 | | | | | | |
| 71 | 3-COOMe | 1 | H | H | 6 | 6 | 6 | 8 | 8 | 9 | | | | | | |
| | | | | | 7 | 7 | 7 | 5 | 5 | 6 | | | | | | |
| 72 | 3-COOEt | 1 | H | H | | | | 5 | 5 | 9 | | | | | | |
| 73 | 3-COO-i-Pr | 1 | H | H | | | | 9 | 9 | 9 | | | | | | |
| 74 | 3-COO-n-Bu | 1 | H | H | 5 | 5 | 6 | 2 | 4 | 9 | 9 | 9 | 9 | | | |
| | | | | | 7 | 7 | 7 | 6 | 6 | 6 | | | | | | |
| 75 | 3-COO-n-Hexyl | 1 | H | H | | | | 7 | 7 | 7.5 | | | | | | |
| 76 | 3-COOMe | 1 | H | 4-Br | | | | 4 | 4 | 9 | 8 | 8 | 7 | | | |
| | | | | | | | | | | | 9 | 9 | 9 | | | |
| 77 | 4-COOH | 1 | H | H | 6.5 | 6.5 | 7.5 | 6 | 6 | 6 | | | | | | |
| | | | | | 5 | 5 | 6 | 7 | 7 | 7 | | | | | | |
| | | | | | 7 | 7 | 7 | | | | | | | | | |
| 78 | 4-COOH | 1 | H | 4-Br | | | | 6 | 6 | 9 | 7 | 7 | 7 | | | |
| | | | | | | | | 8 | 8 | 9 | | | | | | |
| 79 | 4-COOH | 1 | H | 4-Me | 3 | 3 | 6 | 7.5 | 7.5 | 8.5 | 9 | 9 | 9 | | | |
| | | | | | 7 | 7 | 6 | 6 | 6 | 6 | | | | | | |
| 80 | 4-COOH | 1 | 3-Me | H | 5 | 5 | 7 | 6 | 6 | 6 | | | | | | |
| | | | | | 6 | 6 | 6 | 8 | 8 | 7.5 | | | | | | |
| 81 | 4-COOH | 1 | 3-Me | 3-Me | 6 | 6 | 6 | 8.5 | 8.5 | 7.5 | | | | | | |
| | | | | | 7 | 7 | 7 | 6 | 6 | 6 | | | | | | |
| | | | | | | | | 7 | 7 | 7 | | | | | | |
| 82 | 4-COOMe | 1 | H | H | 0 | 4 | 7.5 | 7 | 7 | 7.5 | 7 | 7 | 8 | | | |

TABLE I-continued

| NO | Q | x | $(R_1)_m$ | $(R_2)_n$ | RATE (p.p.m.) 40 A | 40 B | 40 C | 20 A | 20 B | 20 C | 10 A | 10 B | 10 C | 4 A | 4 B | 4 C |
|---|---|---|---|---|---|---|---|---|---|---|---|---|---|---|---|---|
| 83 | 4-COOMe | 1 | 2,6-diNH$_2$ | 4-OMe | 0 8 | 3 8 | 6.5 8 | | | | | | | | | |
| 84 | 2-COOH | 0 | H | H | 3 7 | 3 7 | 6 7 | 8 6 9 6 | 8 6 9 6 | 7.5 6 9 6 | 7 7 | 7 7 | 5 7.5 | | | |
| 85 | 2-COOH | 0 | H | 2-Cl | | | | | | | | | | | | |
| 86 | 2-COOH | 0 | H | 2-Br | 5 7 | 5 7 | 6 7 | 8.5 6 | 8.5 6 | 7.5 7.5 | | | | | | |
| 87 | 2-COOH | 0 | H | 4-Me | 0 | 3.5 | 7.5 | 7 | 7 | 7.5 | 6 | 6 | 7.5 | | | |
| 88 | 2-COOH | 0 | H | 2-OCMe | | | | 7 | 7 | 7 | | | | | | |
| 89 | 2-COOH | 0 | H | 2-CN | | | | 7 | 7 | 7 | | | | | | |
| 90 | 2-COOH | 0 | 2-OMe | H | | | | 6 | 6 | 7 | 8 | 8 | 7 | | | |
| 91 | 2-COOH | 0 | 4-Cl | H | 0 | 3 | 8 | 0 3 | 0 3 | 6 7 | 1.5 6 | 3 6 | 7.5 6 | 7.5 | 7.5 | 7.5 |
| 92 | 2-COOH | 0 | 4-Cl | 2,5-diCl | | | | 4 4 | 4 4 | 6 7 | 6 7 | 6 7 | 6 7 | | | |
| 93 | 2-COOH | 0 | 4-Br | H | 6 7 | 6 7 | 6 7 | 6 7 | 6 7 | 6 7 | | | | | | |
| 94 | 2-COOH | 0 | 4-I | H | 0 0 | 2.5 2.5 | 7.5 7 | 3 | 3 | 8.5 | 0 0.5 5 | 3 2 5 | 7.5 7.5 8.5 | 6.5 | 6.5 | 7.5 |
| 95 | 2-COOH | 0 | 4-I | 2-Me | | | | 1 2 | 1 2 | 7 8.5 | 1 6 | 1 6 | 7 8.5 | | | |
| 96 | 2-COOH | 0 | 4-OH | 2-Me | | | | 1 | 1 | 7 | 6 | 6 | 7 | | | |
| 97 | 2-COOH | 0 | 4-OH | 4-OH | | | | 7 | 7 | 7 | | | | | | |
| 98 | 2-COOH | 0 | 3-OH, 5-OMe | 2-Me, 4,5-diOH | | | | 7 | 7 | 7 | | | | | | |
| 99 | 2-COOMe | 0 | 4-I | H | 5 7 | 5 7 | 6 7 | 9 9 | 9 9 | 9 9 | | | | | | |
| 100 | 2-COOMe | 0 | 4-NH$_2$ | 2-Me | | | | 7 | 7 | 7 | | | | | | |
| 101 | 2-COOMe | 0 | 4-I | 2-Me | | | | 6 | 6 | 7 | 7 | 7 | 7 | | | |
| 102 | 3-COOH | 0 | H | H | | | | 8 | 8 | 8.5 | 9 | 9 | 8.5 | | | |
| 103 | 3-COOH | 0 | 4-OH | H | | | | 0 8 | 3 8 | 7 9 | 8 | 8 | 9 | | | |
| 104 | 3-COOH | 0 | 2-OH | H | | | | 6 | 6 | 7 | | | | | | |
| 105 | 3-COOH | 0 | 4-OOCMe | 4-F | | | | 3 | 3 | 7 | | | | | | |
| 106 | 3-COOH | 0 | 4-OH, 5-Br | H | | | | 7 | 7 | 7 | | | | | | |
| 107 | 4-COOH | 0 | H | H | 0 | 5 | 8 | 1.5 0 2 2 | 3.5 0 2 2 | 7.5 7 7 8.5 | 6 6 7 0 | 6 6 7 0 | 7.5 7 8.5 7 | 5 | 5 | 7 |
| 108 | 4-COOH | 0 | H | 4-Br | | | | 6 0 | 6 0 | 8.5 5 | 7 7 | 7 7 | 8.5 7.5 | | | |
| 109 | 4-COOH | 0 | H | 4-Cl | | | | 2 | 4 | 8.5 | | | | | | |
| 110 | 4-COOH | 0 | H | 4-Me | | | | 6 | 6 | 7 | | | | | | |
| 111 | 4-COOH | 0 | H | 4-NH$_2$ | | | | 5 | 5 | 7 | | | | | | |
| 112 | 4-COOH | 0 | H | 2-NH$_2$ | | | | 3 3 | 3 3 | 8.5 7 | 7 5 | 7 5 | 8.5 7 | | | |
| 113 | 4-COOH | 0 | 3-Me | H | | | | | | | | | | | | |
| 114 | 4-COOH | 0 | 3-Me | 3-Me | | | | | | | | | | | | |
| 115 | 4-COOH | 0 | 3-Cl | 3-Cl, 4-NH$_2$ | 7 | 7 | 7.5 | | | | | | | | | |
| 116 | 3-CHO | 1 | H | H | 0.25 | 3.5 | 8 | 0.5 2 8 | 3 2 8 | 7.5 7 9 | 2 7 | 2.5 7 | 7.5 7 | 6 | 6 | 7.5 |
| 117 | 3-CHO | 1 | 4-Br | H | | | | 6 | 6 | 7 | 6 | 6 | 7 | | | |
| 118 | 2-CHO | 1 | 3-Cl | 2-Cl | | | | 3 | 5 | 8.5 | | | | | | |
| 119 | 2-CHO | 1 | 4-Cl | 2-Me | | | | 7 | 7 | 7.5 | | | | | | |
| 120 | 2-CHO | 1 | 4-CH$_3$ | 2-Cl | | | | 9 0 7 | 9 0 7 | 9 7 9 | | | | | | |
| 121 | 4-CHO | 1 | H | H | | | | 9 | 9 | 9 | | | | | | |
| 122 | 4-CHO | 1 | H | 4-Br | | | | | | | | | | | | |
| 123 | 4-CHO | 1 | 2,6-diI | 4-OMe | | | | 5 | 5 | 7 | | | | | | |

EXAMPLE 11

This Example gives the antagonist performance of various of the Compounds against standard herbicides on soyabean. Method 1 with the modifications indicated was employed. The results are shown in Table IIA (triazine and urea herbicides and Compound 8 as antagonist) and Table IIB (other herbicides and various antagonists).

TABLE IIA

| Herbicide | Herbicide Rate | No Antagonist | Plus Antagonist |
|---|---|---|---|
| Monuron | $5 \times 10^{-7}$ | 0.3 | — |
| | $1 \times 10^{-6}$ | 2.7 | 0 |

TABLE IIA-continued

| Herbicide | Herbicide Rate | No Antagonist | Plus Antagonist |
|---|---|---|---|
| | $2 \times 10^{-6}$ | 7.7 | 1.7 |
| | $4 \times 10^{-6}$ | 9.3 | 6.7 |
| | $8 \times 10^{-6}$ | 10.0 | 10 |
| | $16 \times 10^{-6}$ | — | 10 |
| Diuron | $5 \times 10^{-7}$ | 0 | — |
| | $1 \times 10^{-6}$ | 2.7 | 0 |
| | $2 \times 10^{-6}$ | 6.3 | 0 |
| | $4 \times 10^{-6}$ | 9.7 | 0.7 |
| | $8 \times 10^{-6}$ | 10.0 | 7.0 |
| | $16 \times 10^{-6}$ | — | 9.7 |
| Linuron | $1 \times 10^{-6}$ | 0 | — |
| | $2 \times 10^{-6}$ | 0 | 0 |
| | $4 \times 10^{-6}$ | 2 | 0.7 |
| | $8 \times 10^{-6}$ | 7.3 | 1.0 |
| | $16 \times 10^{-6}$ | 10.0 | 2.3 |
| | $32 \times 10^{-6}$ | — | 9.7 |
| Fluometuron | $5 \times 10^{-7}$ | 0 | — |
| | $1 \times 10^{-6}$ | 0 | 0 |
| | $2 \times 10^{-6}$ | 1.3 | 0.3 |
| | $4 \times 10^{-6}$ | 6.0 | 0.3 |
| | $8 \times 10^{-6}$ | 9.0 | 4.3 |
| | $16 \times 10^{-6}$ | — | 7.7 |
| Methabenz-thiazuron | $2 \times 10^{-6}$ | 0 | — |
| | $4 \times 10^{-6}$ | 0 | 0.3 |
| | $8 \times 10^{-6}$ | 5.3 | 0 |
| | $16 \times 10^{-6}$ | 9.3 | 2.7 |
| | $32 \times 10^{-6}$ | 10.0 | 8.7 |
| | $64 \times 10^{-6}$ | — | 10.0 |
| Noruron | $1 \times 10^{-6}$ | 0 | — |
| | $2 \times 10^{-6}$ | 0.7 | 0.3 |
| | $4 \times 10^{-6}$ | 5.0 | 0.3 |
| | $8 \times 10^{-6}$ | 9.3 | 6.3 |
| | $16 \times 10^{-6}$ | 10.0 | 8.7 |
| | $32 \times 10^{-6}$ | — | 10.0 |
| Chlortoluron | $5 \times 10^{-7}$ | 0 | — |
| | $1 \times 10^{-6}$ | 0.7 | 0 |
| | $2 \times 10^{-6}$ | 5.0 | 0.3 |
| | $4 \times 10^{-6}$ | 8.3 | 0.3 |
| | $8 \times 10^{-6}$ | 9.7 | 6.0 |
| | $16 \times 10^{-6}$ | — | 9.7 |
| Simazine | $1 \times 10^{-6}$ | 1.0 | — |
| | $2 \times 10^{-6}$ | 5.3 | 0.3 |
| | $4 \times 10^{-6}$ | 9.0 | 0.7 |
| | $8 \times 10^{-6}$ | 10.0 | 4.0 |
| | $16 \times 10^{-6}$ | 10.0 | 9.7 |
| | $32 \times 10^{-6}$ | — | 10.0 |
| Atrazine | $1 \times 10^{-6}$ | 2.3 | — |
| | $2 \times 10^{-6}$ | 8.7 | 0 |
| | $4 \times 10^{-6}$ | 10.0 | 6 |
| | $8 \times 10^{-6}$ | 10.0 | 10.0 |
| | $16 \times 10^{-6}$ | 10.0 | 10.0 |
| | $32 \times 10^{-6}$ | — | 10.0 |
| Terbutryne | $2 \times 10^{-6}$ | 1.0 | — |
| | $4 \times 10^{-6}$ | 4.0 | 1.0 |
| | $8 \times 10^{-6}$ | 9.3 | 2.3 |
| | $16 \times 10^{-6}$ | 10.0 | 6.3 |
| | $32 \times 10^{-6}$ | 10.0 | 9.7 |
| | $64 \times 10^{-6}$ | — | 10.0 |
| Cyanazine | $2 \times 10^{-6}$ | 9.0 | — |
| | $4 \times 10^{-6}$ | 10.0 | 0.7 |
| | $8 \times 10^{-6}$ | 10.0 | 0.7 |
| | $16 \times 10^{-6}$ | 10.0 | 9.3 |
| | $32 \times 10^{-6}$ | 10.0 | 10.0 |
| | $64 \times 10^{-6}$ | — | 10.0 |
| Ametryne | $1 \times 10^{-6}$ | 0.3 | — |
| | $2 \times 10^{-6}$ | 4.3 | 0 |
| | $4 \times 10^{-6}$ | 9.0 | 1.0 |
| | $8 \times 10^{-6}$ | 10.0 | 8.7 |
| | $16 \times 10^{-6}$ | 10.0 | 10.0 |
| | $32 \times 10^{-6}$ | — | 10.0 |
| Prometryne | $1 \times 10^{-6}$ | 0 | — |
| | $2 \times 10^{-6}$ | 1.0 | 0.3 |
| | $4 \times 10^{-6}$ | 7.3 | 1.3 |
| | $8 \times 10^{-6}$ | 10.0 | 2.3 |
| | $16 \times 10^{-6}$ | 10.0 | 8.7 |
| | $32 \times 10^{-6}$ | — | 9.7 |
| Aziprotryne | $1 \times 10^{-6}$ | 0.7 | — |
| | $2 \times 10^{-6}$ | 1.7 | 0 |
| | $4 \times 10^{-6}$ | 7.7 | 0.3 |
| | $8 \times 10^{-6}$ | 10.0 | 6.0 |
| | $16 \times 10^{-6}$ | 10.0 | 10.0 |
| | $32 \times 10^{-6}$ | — | 10.0 |

Notes:
(a) A mean of 3 replicates used.
(b) The herbicide application rates are quoted in terms of final pot molarity.
(c) Assessment was made after 14 days.
(d) A scale of 0 (no damage) to 10 (complete kill) was used.

TABLE IIB

| Herbicide | Herbicide Rate (ppm) | Antagonist Compound No | Rate (ppm) | No Antagonist | Plus Antagonist |
|---|---|---|---|---|---|
| Velpar* | 0.4 | 6 | 20 | 9 | 0.5 |
| | | 8 | 20 | | 1.0 |
| 3,5,6-Tribromo-2-fluoro-4-hydroxypyridine+ | 20 | 8 | 20 | 9 | 3 |
| | | 22 | 20 | | 5 |
| | 5 | 22 | 10 | 8 | 0 |
| | | | 20 | | 0 |
| | 10 | | 10 | 8 | 0 |
| | | | 20 | | 0 |
| | 20 | | 10 | 9 | 8 |
| | | | 20 | | 6 |
| Haloxydine+ | 2 | 8 | 20 | 7 | 2 |
| | | 22 | 20 | | 2 |
| 1-methyl-3-phenyl-5-(3-trifluoro-methyl-phenyl)-4(1H)-pyridone° | 0.5 | 22 | 40 | 8 | 0 |
| | | | 10 | | 5 |
| | 1.0 | | 40 | 8 | 4 |
| | | | 10 | | 6 |
| Metflurazone° | 4 | 22 | 40 | 7.5 | 0 |
| | | | 10 | | 0 |
| | 8 | | 40 | 8 | 0 |
| | | | 10 | | 5 |
| Pyrazone× | 0.25 | 22 | 20 | 2 | 0 |
| | 0.5 | | | 4 | 0 |
| | 1.0 | | | 5 | 0.5 |
| | 2.0 | | | 7.5 | 4 |
| | 4.0 | | | 9 | 8 |

TABLE IIB-continued

| Herbicide | Herbicide Rate (ppm) | Antagonist Compound No | Rate (ppm) | No Antagonist | Plus Antagonist |
|---|---|---|---|---|---|
| | 0.25 | | 40 | 2 | 0 |
| | 0.5 | | | 4 | 0 |
| | 1.0 | | | 5 | 0 |
| | 2.0 | | | 7.5 | 0.5 |
| | 4.0 | | | 9 | 3.5 |

*Method 1
+Method 1 but assessment after 14 days
ºMethod 1 but assessment after 12 days
ˣMethod 1 but assessment after 7 days

EXAMPLE 12

The antagonist compounds were tested on cotton and on French beans (The Prince variety) for their antagonist activity on atrazine and/or diuron. Method 1 was used with the modifications (made because of slower propagation) that the plants were treated 7 days after sowing and the plants were assessed after 21 days (cotton) and after 10 and 17 days (French beans). The results are shown in Table IIIA (cotton) and IIIB (French beans).

TABLE IIIA

| Herbicide | Herbicide Rate (ppm) | Antagonist Compound No | (ppm) | No Antagonist | Plus Antagonist |
|---|---|---|---|---|---|
| Diuron | 4 | 22 | 20 | 7 | 7 |
| | | | 100 | | 3* |
| | | 107 | 20 | | 2 |
| | | | 100 | | 3* |

TABLE IIIA-continued

| Herbicide | Herbicide Rate (ppm) | Antagonist Compound No | (ppm) | No Antagonist | Plus Antagonist |
|---|---|---|---|---|---|
| | | 23 | 20 | | 6 |
| | | | 100 | | 4* |
| Atrazine | 2 | 22 | 20 | 5 | 0 |
| | | | 100 | | 3* |
| | | 107 | 20 | | 0 |
| | | | 100 | | 4* |
| | | 23 | 20 | | 0 |
| | | | 100 | | 4* |

*Score = phytotoxic effect of high rate of antagonist, no herbicide effects apparent

TABLE IIIB

| DIURON RATE (ppm) | ANTAGONIST COMPOUND NO | RATE (ppm) | 10 DAY ASSESSMENT* | | | 17 DAY ASSESSMENT* | | |
|---|---|---|---|---|---|---|---|---|
| | | | REP A | REP B | MEAN | REP A | REP B | MEAN |
| 0 | — | — | 0 | 0 | 0 | 0 | 0 | 0 |
| 0.375 | — | — | 1 | 0.5 | 0.75 | 0.5 | 0 | 0.25 |
| 0.75 | — | — | 3 | 5 | 4 | 3 | 6 | 4.5 |
| 1.5 | — | — | 7 | 9 | 8 | 8 | 9 | 8.5 |
| 0 | 4 | 40 | 2 (st) | 1 (st) | 1.5 (st) | 2 (st) | 0 | 1 (st) |
| 0.375 | 4 | 40 | 0 | 1 (st) | 0.5 (st) | 0 | 0 | 0 |
| 0.75 | 4 | 40 | 1 (st) | 2 (st) | 1.5 (st) | 1 (st) | 2 (st) | 1.5 (st) |
| 1.5 | 4 | 40 | 0 | 0 | 0 | 0 | 0 | 0 |
| 0 | 5 | 40 | 0 | 1 (st) | 0.5 (st) | 2 (st) | 0 | 1 (st) |
| 0.375 | 5 | 40 | 0 | 1 (st) | 0.5 (st) | 0 | 0 | 0 |
| 0.75 | 5 | 40 | 0.5 | 0.5 | 0.5 | 0.5 | 2 | 1.25 |
| 1.5 | 5 | 40 | 1 | 0.5 | 0.75 | 3 | 4 | 3.5 |

*Days post Diuron Treatment
(St) = Stunt, phytotoxic effect of antagonist
REP = Replicate

EXAMPLE 13

The antagonist activity and selectivity of various of the compounds of general formula (I) were tested on various herbicides. The results are shown in Tables IVA (atrazine), IVB (diuron), IVC (cyanazine), IVD (haloxydine), IVE (velpar) and IVF (cyanazine).

TABLE IVA

| | | SPECIES + ATRAZINE RATE (KG/HA) | | | | | | | | | | | | | | | | | | | | |
|---|---|---|---|---|---|---|---|---|---|---|---|---|---|---|---|---|---|---|---|---|---|---|
| | | SOYBEAN | | | | SETARIA VIRIDIS | | | | | DIGITARIA SANGUINALIS | | | | | AMARANTHUS RETROFLEXUS | | | | | ABUTILON THEOPHRASTI | | | |
| Compound No | Rate (kg/ha) | 0 | 0.5 | 1 | 3 | 5 | 0 | 0.5 | 1 | 3 | 5 | 0 | 0.5 | 1 | 3 | 5 | 0 | 0.5 | 1 | 3 | 5 | 0 | 0.5 | 1 | 3 | 5 |
| Nil | — | 0 | 4 | 8.5 | 9 | 9 | 0 | 4.5 | 5 | 8.5 | 8.5 | 0 | 6.5 | 7 | 8.5 | 9 | 0 | 9 | 9 | 9 | 9 | 0 | 6.5 | 7 | 8.5 | 9 |
| 6 | 10 | 0 | 0.5 | 2 | 7 | 9 | 1 | 5.5 | 7 | 7.5 | 8.5 | 0 | 5 | 8 | 8.5 | 9 | 5.5 | 9 | 9 | 9 | 9 | 0 | 2.5 | 1.5 | 5.5 | 7.5 |
| 8 | 10 | 0 | 0 | 2.5 | 9 | 9 | 0 | 6.5 | 7 | 8.5 | 8 | 2 | 4.5 | 7 | 7.5 | 8.5 | 5 | 9 | 9 | 9 | 9 | 0 | 1.5 | 5.5 | 7 | 9 |
| 1 | 10 | 0 | 1 | 9 | 9 | 9 | 0 | 7 | 8 | 8.5 | 9 | 1.5 | 4 | 6.5 | 9 | 9 | 6 | 9 | 9 | 9 | 9 | 0 | 4 | 4.5 | 6.5 | 9 |
| 1 | 40 | 0 | 0 | 1 | 2 | 9 | 6 | 7 | 7.5 | 8 | 9 | 6 | 6 | 7.5 | 8 | 9 | 9 | 9 | 9 | 9 | 9 | — | 6 | 7.5 | 7 | 8.5 |

Method 2

TABLE IVB

| | | SPECIES + DIURON RATE (KG/HA) | | | | | | | | | | | | | | | | | | | | | | | |
|---|---|---|---|---|---|---|---|---|---|---|---|---|---|---|---|---|---|---|---|---|---|---|---|---|---|
| Compound No | Rate (Kg/ha) | SOYBEAN | | | | | SETARIA VIRIDIS | | | | | DIGITARIA SANGUINALIS | | | | | AMARANTHUS RETROFLEXUS | | | | | ABUTILON THEOPHRASTI | | | | |
| | | 0 | 0.5 | 1 | 3 | 5 | 0 | 0.5 | 1 | 3 | 5 | 0 | 0.5 | 1 | 3 | 5 | 0 | 0.5 | 1 | 3 | 5 | 0 | 0.5 | 1 | 3 | 5 |
| Nil | — | 0 | 0.5 | 7.5 | 8.5 | 9 | 0 | 4.5 | 5 | 8.5 | 8.5 | 0 | 6.5 | 7 | 8.5 | 9 | 0 | 9 | 9 | 9 | 9 | 0 | 6.5 | 7 | 8.5 | 9 |
| 6 | 10 | 0 | 0 | 0 | 0 | 9 | 1 | 6.5 | 9 | 9 | 9 | 0 | 7.5 | 9 | 9 | 9 | 5.5 | 8.5 | 9 | 9 | 9 | 0 | 0 | 0.5 | 8 | 9 |
| 8 | 10 | 0 | 0 | 0 | 0.5 | 6.5 | 0 | 4 | 9 | 9 | 9 | 2 | 4.5 | 9 | 9 | 9 | 5 | 9 | 9 | 9 | 9 | 0 | 0 | 2 | 8.5 | 9 |
| 1 | 10 | 0 | 0 | 1.5 | 9 | 9 | 0 | 7 | 9 | 9 | 9 | 1.5 | 9 | 9 | 9 | 9 | 6 | 9 | 9 | 9 | 9 | 0 | 2.5 | 4 | 9 | 9 |
| 1 | 40 | 0 | 0 | 0 | 0.5 | 8 | 6 | 8 | 9 | 9 | 9 | 6 | 7 | 8 | 9 | 9 | 9 | 9 | 9 | 9 | 9 | — | 8 | 8 | 8 | 8.5 |

Method 2

TABLE IVC

| | | SPECIES + CYANAZINE RATE (KG/HA) | | | | | | | | | | | | | | | | | | | | | | | |
|---|---|---|---|---|---|---|---|---|---|---|---|---|---|---|---|---|---|---|---|---|---|---|---|---|---|
| Compound No | Rate (Kg/ha) | SOYBEAN | | | | | SETARIA VIRIDIS | | | | | DIGITARIA SANGUINALIS | | | | | AMARANTHUS RETROFLEXUS | | | | | XANTHIUM SPINOSUM | | | | |
| | | 0 | 0.5 | 1 | 2 | 4 | 0 | 0.5 | 1 | 2 | 4 | 0 | 0.5 | 1 | 2 | 4 | 0 | 0.5 | 1 | 2 | 4 | 0 | 0.5 | 1 | 2 | 4 |
| Nil | — | 0 | 0 | 8.5 | 10 | 10 | 0 | 6 | 10 | 10 | 10 | 0 | 8 | 10 | 10 | 10 | 0 | 4 | 8 | 9 | 10 | 0 | 10 | 10 | 10 | 9.5 |
| 8 | 10 | 0 | 0 | 0 | 0 | 1.5 | 3 | 4 | 4 | 8 | 10 | 0 | 0 | 7.5 | 10 | 10 | 4.5 | 6.5 | 6.5 | 8.5 | 10 | 0 | 4.5 | 10 | 10 | 10 |
| 8 | 20 | 0 | 0 | 0.5* | 0.5* | 0.5* | 5 | 6.5 | 8.5 | 8.5 | 8.5 | 0 | 8 | 8 | 10 | 10 | 7.5 | 8.0 | 8.5 | 9.0 | 10 | 0 | 3 | 6.5 | 10 | 10 |

*Phytotoxic effect (stunting) produced by high rate antagonist treatment (no herbicide effects apparent)
Method 2 except that the crops and weeds grown in rows in single 35 cm. seed trays; assessment on 0–10 scale.

TABLE IVD

| | | SPECIES + HALOXYDINE RATE (KG/HA) | | | | | | | | | | | | | | |
|---|---|---|---|---|---|---|---|---|---|---|---|---|---|---|---|---|
| Compound No | Rate (Kg/ha) | SOYBEAN | | | SETARIA VIRIDIS | | | DIGITARIS SANGUINALIS | | | AMARANTHUS RETROFLEXUS | | | XANTHIUM SPINOSUM | | |
| | | 0.25 | 0.5 | 1 | 0.25 | 0.5 | 1 | 0.25 | 0.5 | 1 | 0.25 | 0.5 | 1 | 0.25 | 0.5 | 1 |
| Nil | — | 2 | 4.5 | 8 | 3 | 7.5 | 9 | — | 4 | 6.5 | 4 | 7 | 5 | 0 | 0 | 0 |
| 8 | 10 | 0 | 0 | 0.25 | 0 | 3.5 | 8 | 4 | 5 | 8 | 8 | 8 | 8.5 | 0 | 0 | 0 |
| 8 | 20 | 0 | 0 | 0 | 0 | 2 | 5.5 | 0 | 5.5 | 4.5 | 7.5 | 7 | 8 | 0 | 0 | 0 |

Method 2

TABLE IVE

| | | SPECIES + VELPAR RATE (KG/HA) | | | | | | | | | | | |
|---|---|---|---|---|---|---|---|---|---|---|---|---|---|
| Compound No | Rate (Kg/ha) | SOYBEAN | | | SETARIA VIRIDIS | | | IPOMEA PURPUREA | | | AMARANTHUS RETROFLEXUS | | | XANTHIUM SPINOSUM | | |
| | | 0.2 | 0.4 | 0.8 | 0.2 | 0.4 | 0.8 | 0.2 | 0.4 | 0.8 | 0.2 | 0.4 | 0.8 | 0.2 | 0.4 | 0.8 |
| Nil | — | 8 | 9 | 9 | 5.5 | 8.5 | 8.5 | 8.5 | 9 | 9 | 4 | 8.5 | 8 | 2.5 | 9 | 9 |
| 8 | 10 | 4.5 | 8 | 9 | 5.5 | 8.5 | 9 | 8 | 9 | 9 | 1 | 7.5 | 8.5 | 3.5 | 8.5 | 9 |

Method 2

TABLE IVF

| | | SPECIES + CYANANZINE [RATE = KG/HA] | | | | | | | | | | |
|---|---|---|---|---|---|---|---|---|---|---|---|---|
| Compound No | Rate (Kg/ha) | Soybean | Portulaca Oleracea | Amaranthus Retroflexus | Ipomea Purpurea | Demsmodium Tortusosum | Abutilon Theophrasti | Sesbania Exaltata | Cassia Obtusi Folia | Sida Spinosa | Datura stra- Monium | Xanthium Pensyl- Vaticum |
| 8 | 1 | 5 | 9 | 6 | 8 | 9 | 9 | 9 | 2 | 9 | 9 | 9 |
| | 2 | 2 | 9 | 8 | 8 | 8 | 8 | 9 | 2 | 9 | 9 | 8 |
| | 4 | 1 | 9 | 8 | 8 | 8 | 8 | 9 | 2 | 9 | 9 | 9 |
| 22 | 1 | 6 | 9 | 8 | 9 | 9 | 9 | 9 | 3 | 9 | 9 | 9 |
| | 2 | 3 | 9 | 7 | 9 | 9 | 9 | 9 | 2 | 9 | 9 | 9 |
| | 4 | 0 | 9 | 7 | 9 | 9 | 9 | 9 | 1 | 9 | 9 | 8 |

EXAMPLE 14

This Example shows the effect of applying the antagonist (Compound 8; rate 20 ppm) before, simultaneously with and after, the application of the herbicide (cyanazine or diuron). Method 1 was used. The crop was soybean. The results are shown in Table V.

TABLE V

| ANTAGONIST APPLICATION | CYANAZINE RATE(Mol) | | | | | DIURON RATE (Mol) | | | | |
|---|---|---|---|---|---|---|---|---|---|---|
| | 0 | $2 \times 10^{-6}$ | $4 \times 10^{-6}$ | $8 \times 10^{-6}$ | $16 \times 10^{-6}$ | 0 | $1 \times 10^{-6}$ | $2 \times 10^{-6}$ | $4 \times 10^{-6}$ | $8 \times 10^{-6}$ |
| Nil | 0 | 1.3 | 9. | 10 | 10 | 0 | 0.7 | 5.7 | 9.7 | 10 |
| 3 days pre herbicide application | 0 | 0 | 0 | 0 | 1.7 | 0.3* | 0 | 0 | 0.3 | 3 |
| 1 day pre herbicide application | 0 | 0 | 0 | 1 | 8.7 | 0 | 0 | 0 | 1 | 9 |
| Simultaneous with |  |  |  |  |  |  |  |  |  |  |

TABLE V-continued

| ANTAGONIST APPLICATION | CYANAZINE RATE(Mol) | | | | | DIURON RATE (Mol) | | | | |
|---|---|---|---|---|---|---|---|---|---|---|
| | 0 | $2 \times 10^{-6}$ | $4 \times 10^{-6}$ | $8 \times 10^{-6}$ | $16 \times 10^{-6}$ | 0 | $1 \times 10^{-6}$ | $2 \times 10^{-6}$ | $4 \times 10^{-6}$ | $8 \times 10^{-6}$ |
| herbicide application | 0 | 0 | 0 | 0.7 | 8.3 | 0 | 0 | 1.3 | 1.7 | 6.7 |
| 1 day post herbicide application | 0 | 0 | 0 | 0.7 | 9 | 0 | 0 | 0 | 2 | 10 |
| 3 days post herbicide application | 0.7* | 0 | 1.7 | 9.7 | 10 | 0 | 0.7 | 3.7 | 8 | 10 |

*phytotoxic stunt produced by antagonist treatment

EXAMPLE 15

This Example shows that the method of the invention is versatile in that the antagonist (Compound 22; applied at 10 kg/ha) and the herbicide (atrazine or cyanazine) can be sprayed on the soil surface or incorporated in the soil. Method 2 was used. The crop was soybean. The results are shown in Table VI.

| | % w/w |
|---|---|
| Calcium salt of Compound 22 | 72.0 |
| Vanisperse CB | 2.8 |
| Aerosol OT-B | 1.1 |
| Spestone | 24.1 |

TABLE VI

| ANTAGONIST TREATMENT | SURFACE SPRAYED- ATRAZINE | | SURFACE SPRAYED- CYANAZINE | | INCORPORATED- ATRAZINE | | INCORPORATED- CYANAZINE | |
|---|---|---|---|---|---|---|---|---|
| | 0.5 Kg/ha | 1.0 Kg/ha | 1.0 Kg/ha | 2.0 Kg/ha | 0.25 Kg/ha | 0.5 Kg/ha | 0.5 Kg/ha | 1.0 Kg/ha |
| Nil | 1.7 | 9 | 6 | 8.3 | 0.3 | 6.6 | 2 | 7.7 |
| Surface Sprayed | 0 | 0.7 | 0 | 0 | 0 | 0 | 0 | 0 |
| Incorporated | 0.3 | 4.3 | 0 | 0 | 0 | 0 | 0 | 0 |

EXAMPLE 16

This Example shows that the antagonist (Compound 22; rate 10 kg/ha) can be applied in just a band along the soybean row with equally good results as when the whole area is treated with the antagonist. Method 2 was used except that the plants were grown in large seed trays. The results are shown in Table VII.

TABLE VII

| ANTOGONIST TREATMENT | DIURON RATE (PPM) | | | |
|---|---|---|---|---|
| | 0 | 0.5 | 1.0 | 2.0 |
| Nil | 0 | 1 | 3.5 | 6.5 |
| Over whole tray | 0.5* | 1.5 | 0.5 | 2.0 |
| Over 5 cm band | 2.0* | 0 | 2.0 | 1.5 |
| Over 10 cm band | 0.5* | 1.0 | 0 | 1.5 |

*Phytotoxic stunt produced by antagonist treatment

EXAMPLE 17

The following compositions were prepared.

1. 50% w/w Dispersible powder containing:

| | % w/w |
|---|---|
| Compound 22 | 50 |
| Vanisperse CB (a liqnosulphonate; dispersant) | 5 |
| Aerosol OT-B (a sulphosuccinate; wetter) | 2 |
| Spestone (china clay; filler) | 43 |

2. 50% w/w Dispersible powder containing:

| | % w/w |
|---|---|
| Sodium salt of Compound 22 | 57.0 |
| Vanisperse CB | 4.3 |
| Aerosol OT-B | 1.7 |
| Spestone | 37.0 |

3. 50% w/w Dispersible powder containing:

4. 50% w/w Dispersible powder containing:

| | % w/w |
|---|---|
| Ammonium salt of Compound 22 | 53.0 |
| Vanisperse CB | 4.7 |
| Aerosol OT-B | 1.9 |
| Spestone | 41.4 |

5. 50% w/w Dispersible powder containing:

| | % w/w |
|---|---|
| Isopropylamine salt of Compound 22 | 61.0 |
| Vanisperse CB | 3.9 |
| Aerosol OT-B | 1.6 |
| Spestone | 34.5 |

6. 20% w/w Emulsifiable concentrate containing:

| | % w/w |
|---|---|
| Synprolam 35 salt of Compound 22 | 35.2 |
| Toximul R (anionic/nonionic surfactant blend, emulsifier) | 3.3 |
| Toximul S (anionic/nonionic surfactant blend, emulsifier) | 6.7 |
| Aromasol H (aromatic hydrocarbon mixture, solvent) | 54.8 |

Synprolam 35 is a mixture of synthetic alkyl amines consisting mostly of $C_{13}H_{27}NH_2$ and $C_{15}H_{31}NH_2$.

7. 10% w/w Aqueous solution containing:

| | % w/w |
|---|---|
| Dimethylamine salt of Compound 22 | 11.6 |
| Water | 88.4 |

Diuron or cyanazine were added to each of these compositions to provide compositions containing the following w/w ratios of diuron or cyanazine to Compound 22:
1:2.5, 1:5, 1:10, 3:25, 3:5 and 3:10.

The diuron used was in the form of a commercial preparation which was a wettable powder containing 80% of active ingredient. The cyanazine used was a commercial formulation called Fortrol (a 50% suspension concentrate).

EXAMPLE 18

The compositions of Example 17 were tested as antagonist compositions using method 2 against diuron and cyanazine on soyabeans. The results are shown in Table VIII.

TABLE VIII

| ANTAGONIST TREATMENT | | DIURON RATE (KG/HA) | | CYANAZINE RATE (KG/HA) | |
|---|---|---|---|---|---|
| COMPOISITON NO | RATE (Kg/ha) | 1 | 3 | 1 | 3 |
| 1 | 2.5 | 6.5 | 9 | 5 | 9 |
|   | 5 | 0.5 | 9 | 3 | 5 |
|   | 10 | 2 | 5.5 | 0.5 | 4 |
| 2 | 2.5 | 2 | 9 | 5.5 | 9 |
|   | 5 | 0.5 | 9 | 0 | 3.5 |
|   | 10 | 0 | 6 | 0.5 | 1 |
| 3 | 2.5 | 4 | 9 | 6.5 | 7.5 |
|   | 5 | 1 | 9 | 5 | 8 |
|   | 10 | 0 | 7 | 0 | 3.5 |
| 4 | 2.5 | 8 | 9 | 9 | 9 |
|   | 5 | 3.5 | 8 | 1 | 2 |
|   | 10 | 0 | 7.5 | 0 | .2 |
| 5 | 2.5 | 1.5 | 9 | 0 | 8 |
|   | 5 | 0 | 9 | 0 | 0 |
|   | 10 | 0 | 4.5 | 0 | 0.5 |
| 6 | 2.5 | 1.5 | 9 | 1 | 3 |
|   | 5 | 5.5 | 8 | 2 | 5.5 |
|   | 10 | 2.5 | 9 | 0 | 0.5 |
| 7 | 2.5 | 7.5 | 9 | 3.5 | 5 |
|   | 5 | 0 | 8.5 | 0 | 3.5 |
|   | 10 | 0 | 2.5 | 0.5 | 0 |
| Herbicide alone as control | — | 7* | 9* | 9* | 9* |

*Mean of 12 replicates, other data mean of 2 replicates.

In the next Example, a different method (Method 4) was used to assess the herbicide antagonism.

METHOD 4 (GLASSHOUSE SOIL INCORPORATION TEST)

A subsoil of Norfolk loamy sand was placed in 20 cm pots and saturated with water. Drainage was allowed for 5 days. When the subsoil moisture level had dropped to approximately 12%, 2000 ml of moist topsoil (Norfolk loamy sand) was added to each pot. Seeds of barnyardgrass (*Echinochloa crus-galli*) were incorporated into the topsoil with a Muller mixer. Compound 9 (at 8.4 kg/ha) was then incorporated in the soil. Soybean seeds (Ransom) were then planted 2.5 cm deep in rows (5 seed/pot).

Twenty four hours after planting, the herbicides were applied to the soil surface using a laboratory sprayer. Each herbicide was applied alone and in combination with the previously incorporated Compound 9. Herbicides were applied with an 8002E nozzle at 30 psi in 40 gpa. All treatments were done in triplicate.

After spraying, the pots were placed in a random fashion in the greenhouse. No water was applied after treatment until the soybeans began cracking the soil surface. At this time watering was begun and for the remainder of the test water was aplied as needed.

An assessment of barnyardgrass injury ratings was made 18 days after treatment, following which the weeds were removed by hand to permit longer term observation of soybean response in the absence of weed competition. Assessment of soybean injury were made at 20, 34, 41 and 57 days after treatment (DAT). All the results are expressed as percentage phytotoxicity in relation to the untreated controls, averaged over three replicates.

EXAMPLE 19

The antagonist activity and selectivity of Compound 9 was tested on atrazine, prometryne and metribuzin using Method 4 (a soil test). Results are shown in Table IVA (Soybean injury) and IVB (barnyardgrass control).

TABLE IVA

| | | % Phytotoxicity on Soybeans | | | | | | | |
|---|---|---|---|---|---|---|---|---|---|
| | | 20 DAT | | 34 DAT | | 41 DAT | | 57 DAT | |
| Treatments | Rate (kg/ha) | − Compound 9 | + Compound 9 | − Compound 9 | + Compound 9 | − Compound 9 | + Compound 9 | − Compound 9 | + Compound 9 |
| Atrazine | 0.33 | 2 | 12 | 2 | 0 | 17 | 5 | 18 | 0 |
|  | 0.66 | 23 | 22 | .78 | 3 | 86 | 8 | 80 | 5 |
|  | 1.12 | 27 | 30 | 53 | 42 | 62 | 43 | 60 | 30 |
| Prometryne | 0.66 | 2 | 3 | 0 | 0 | 0 | 0 | 0 | 0 |
|  | 1.12 | 2 | 0 | 2 | 0 | 7 | 0 | 3 | 0 |
|  | 2.24 | 3 | 3 | 2 | 0 | 17 | 2 | 23 | 0 |
| Metribuzin | 0.33 | 13 | 2 | 20 | 0 | 22 | 0 | 15 | 0 |
|  | 0.66 | 10 | 15 | 55 | 2 | 52 | 17 | 38 | 3 |
|  | 1.12 | 85 | 60 | 87 | 68 | 75 | 72 | 57 | 83 |

TABLE IVB

| Treatments | Rate (kg/ha) | % Phytotoxicity on Barnyardgrass | |
|---|---|---|---|
| | | no Compound 9 | with Compound 9 |
| Atrazine | 0.33 | 3 | 0 |
|  | 0.66 | 33 | 10 |
|  | 1.12 | 83 | 53 |
| Prometryne | 0.66 | 18 | 12 |
|  | 1.12 | 93 | 80 |
|  | 2.24 | 98 | 100 |
| Metribuzin | 0.33 | 38 | 33 |
|  | 0.66 | 97 | 97 |
|  | 1.12 | 100 | 100 |
| Control | — | 0 | 0 |

We claim:

1. A method of protecting a legume or cotton crop in a locus from herbicidal damage, said method consisting essentially of applying to the locus prior to the emergence of the crop, either successively (in either order) or together, (a) a herbicide which is capable of being taken up by a plant from the soil and which is capable of being translocated to a main herbicidal site of action within the foliage of the plant and which operates by interfering with photosynthesis in said plant, and (b) an effective amount of an antidotally active compound of general formula (I):

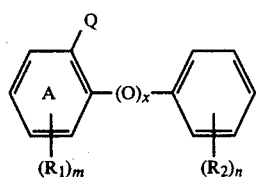

wherein each of $R_1$ and $R_2$, which may be the same or different, is hydrogen, halogen, $C_{1-3}$ alkoxy, $C_{1-4}$ alkyl, trihalomethyl or hydroxy, Q is carboxy or a salt or ester thereof, x is 1, m is 1 or 2 and n is 1 or 2.

2. A method as claimed in claim 1 wherein, in (b), $R_1$ is halogen in the 4-position and Q is carboxy or a sodium, calcium, ammonium or alkylamine salt thereof.

3. A method as claimed in claim 3 wherein the alkylamine is dimethylamine, isopropylamine, tridecylamine or pentadecylamine.

4. A method as claimed in claim 1 wherein (b) is 3-chloro-6-(2'-methylphenoxy)benzoic acid, 3-chloro-6-(2',5'-dimethylphenoxy)benzoic acid, 3-chloro-6-(3',5'-dimethylphenoxy)benzoic acid, 3-chloro-6-(2'-chlorophenoxy)benzoic acid, 3-chloro-6-(3'-chlorophenoxy)benzoic acid, 3-chloro-6-(2'-methoxyphenoxy)benzoic acid, 3-chloro-6-(3'-methoxyphenoxy)benzoic acid, 3-chloro-6-(3',5'-dichlorophenoxy)benzoic acid, 3-chloro-6-(3'-methoxy-5'-chlorophenoxy)benzoic acid or 4-chloro-6-(3',5'-dimethylphenoxy)benzoic acid.

5. A method as claimed in claim 1 wherein (a) is
(1) a triazine herbicide;
(2) a urea herbicide;
(3) a halopyridine of general formula:

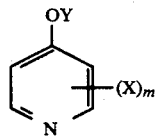

wherein X is hydrogen or halogen, m is an integer of 1 to 4 and Y is hydrogen or aralkyl;
(4) a triazine dione of general formula:

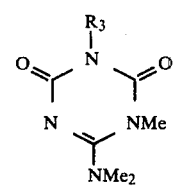

wherein $R_3$ is $C_{3-6}$ alkyl or optionally methyl-substituted $C_{5-8}$ cycloalkyl;
(5) a pyridone of general formula:

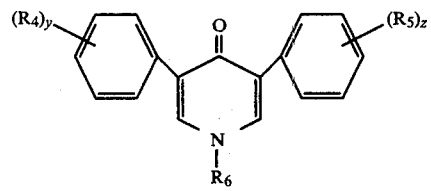

wherein each of $R_4$ and $R_5$, which may be the same or different, is halogen, $C_{1-3}$ alkyl or alkoxy or trifluoromethyl, each of z and y, which may be the same or different, is 0, 1 or 2, and $R_6$ is $C_{1-3}$ alkyl, $C_{2-3}$ alkenyl, acetoxy or methoxy; or
(6) a pyridazinone of general formula:

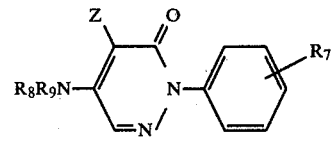

wherein Z is halogen (e.g. fluorine, chlorine or bromine), $R_7$ is hydrogen or trihalomethyl, and each of $R_8$ and $R_9$, which may be the same or different, is hydrogen or alkyl.

6. A method as claimed in claim 5 wherein (a) is atrazine, cyanazine, diuron or linuron.

* * * * *